United States Patent [19]
Pleatman

[11] Patent Number: 5,192,284
[45] Date of Patent: Mar. 9, 1993

[54] SURGICAL COLLECTOR AND EXTRACTOR

[76] Inventor: Mark A. Pleatman, 3328 Bloomfield Shore Dr., West Bloomfield, Mich. 48033

[21] Appl. No.: 818,929

[22] Filed: Jan. 10, 1992

[51] Int. Cl.⁵ .............................................. A61B 17/00
[52] U.S. Cl. .................................... 606/114; 606/108; 606/110; 606/127; 604/158
[58] Field of Search ............... 606/108, 110, 113, 114, 606/127, 128; 604/158; 600/37

[56] References Cited

U.S. PATENT DOCUMENTS

| | | | |
|---|---|---|---|
| 30,471 | 10/1860 | Dudley | 606/127 |
| 156,477 | 11/1874 | Bradford | 606/127 |
| 3,472,230 | 10/1969 | Fogarty | 606/127 |
| 4,557,255 | 12/1985 | Goodman | 606/127 |
| 4,997,435 | 3/1991 | Demeter | 606/127 |
| 5,037,379 | 8/1991 | Clayman et al. | 600/37 |
| 5,074,867 | 12/1991 | Wilk | 606/127 |

FOREIGN PATENT DOCUMENTS 0025796  1/1884  Brazil ................................ 606/127

Primary Examiner—Stephen C. Pellegrino
Assistant Examiner—Glenn Dawson
Attorney, Agent, or Firm—Austin R. Miller

[57] ABSTRACT

A surgical collector and extractor for specimem removal through a cannula in a laparoscopic procedure. A flexible sac has an opening adapted for specimem collection. The sac is constructed to expand, when not confined, to form a receptacle having a size larger than the inside of the cannula and being rigid enough to hold its expanded shape. The sac is composed of a collapsible material permitting it to be reduced in size to be accommodated within the cannula.

14 Claims, 1 Drawing Sheet

SURGICAL COLLECTOR AND EXTRACTOR

BACKGROUND OF THE INVENTION

1. Field of the Invention

This invention relates to medical instruments, particularly to a surgical collector and extractor for specimen removal in surgical procedures such as those directed to removal of or operation upon the gall bladder, appendices, ectopic pregnancies, uterine mycmas, ovaries and the like. The invention further relates to a surgical collector and extractor particularly useful for the laparoscopic removal of large specimens, such as those intended to be removed in the foregoing procedures and in others, whether in the gynecological or general surgery fields.

2. Description of the Background

Laparoscopic surgical procedures generally involve the use of one or more small incisions in the body of the patient, with many advantages including minimum trauma to the patient and more rapid and complete recovery from the surgical procedure. Because of their tremendous advantages, laparoscopic surgical procedures have become more and more popular and are expected to be even more widely used in the future.

In the utilization of laparoscopic procedures for removal of large specimens, problems arise because of the difficulty in removing such large specimens through the small incisions utilized in the laparoscopic procedure.

It is accordingly an object of this invention to provide a new and improved surgical collector and extractor for specimen removal, especially in a laparoscopic surgical procedure, and to provide a method for the removal of large specimens through small incisions.

Another object of the invention is to provide an improved surgical collector and extractor for specimen removal in laparoscopic procedures, which can be employed in parts of the body where extractors heretofore available could not be utilized.

Still another object of this invention is to provide a surgical collector and extractor which sometimes allows for removal of large specimens by simply dilating the incision site rather than surgically excising it.

Still another object of this invention is to provide a means which may be utilized during a laparoscopic procedure to remove the entire large specimen together with all of the fluids and tissue to be contained therein.

Still another object of this invention is to provide a sac which can be utilized in a laparoscopic procedure and which is not reflective in a manner to cause blooming on the video screen usually utilized by the surgeon in performing the laparoscopic procedure.

Still another object of this invention is to provide a sac for laparoscopic surgery which is provided with an opening for collection of large specimens and fluids, which protects the operation site from contact with such specimen and fluids, and which provides an open orifice even when the sac is rotated within the abdomen.

Other objects and advantages of this invention, including the ease with which the sac may be automatically opened to remove objects from the human body, will further become apparent hereinafter, and in the drawings, of which:

Description of the Preferred Embodiment

Figure 3:
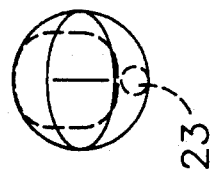
FIG. 3 is an end view of the surgical collector of FIGS. 1 and 2.

Although the following description will be directed to the specific form of the invention selected for illustration in the drawings, it will be appreciated that many features of the invention may be varied and that the invention can be embodied in a wide variety of forms. Accordingly, the description which follows is not intended to define or limit the scope of the invention, which is referred to in the appended claims.

Turning now to the specific form of the invention selected for illustration in the drawings, 10 designates the surgical collector which is adapted to be inserted into and withdrawn from a cannula C or the like, inserted through the wall W of the abdomen or other portion of the human body in the performance of the usual laparoscopic procedure, and which carries a surgical collector and extractor sac 13 in accordance with this invention. Sac 13 has a closed end 14 and an open end 15 which is solvent bonded or heat shrunk at 16 to a body tube 17 which is movable back and forth along the axis of the cannula C. The body tube 17 is preferably hollow as shown and, if so, is sealed at the top with a seal 20.

The sac 13 is composed of flexible sheet material which has the ability to fold upon itself accordion-style to render it sufficiently compact to be contained within the cannula C. However, as will further be developed hereinafter, the sac has a "memory" and is constructed to expand automatically, when not confined, to open up easily within the abdomen to form a receptacle having a size larger than the confining space within the cannula C. When expanded, the sac 13 is rigid enough to hold its expanded shape, as shown.

Figure 1:
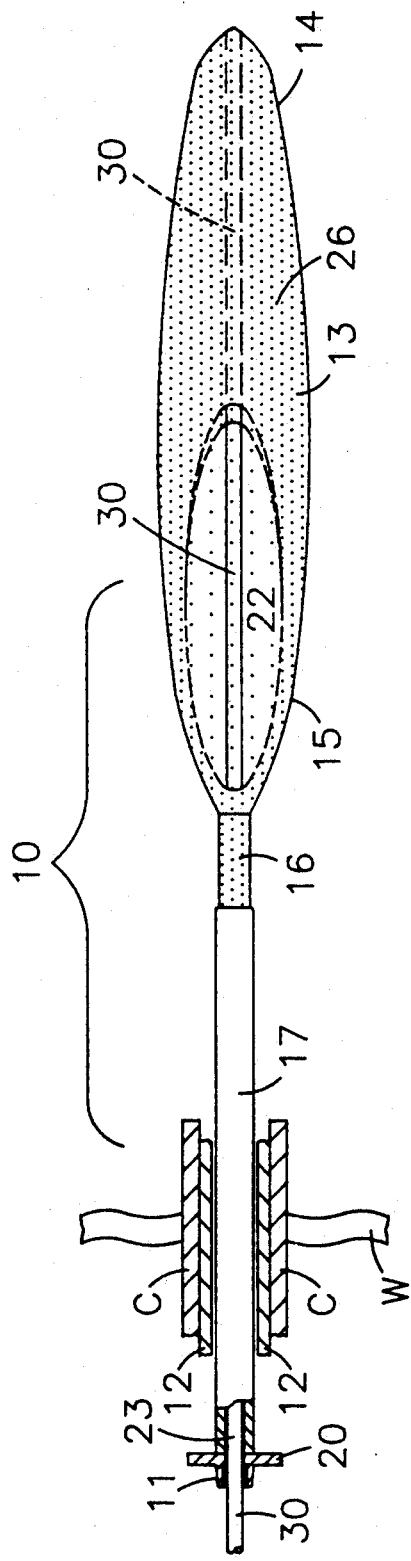
FIG. 1 is a top view of one form of surgical collector and extractor utilizing features of this invention, shown combined with a cannula and positioned in a body incision.
Figure 2:
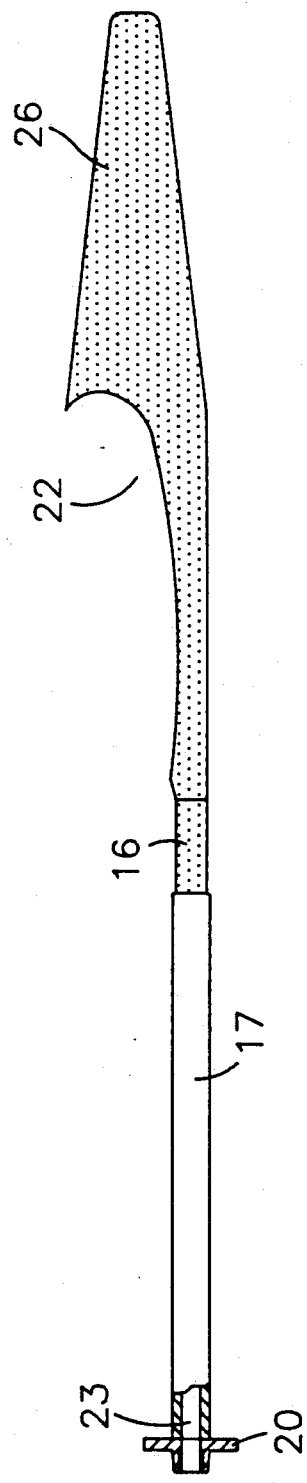
FIG. 2 is a side view of the surgical collector of FIG. 1.

The sac according to FIGS. 1-3 is shown in its expanded condition, having been inserted through an incision in the abdominal wall W, through a conventional cannula C or the like. The cannula may be of any type but is preferably provided with a known self-sealing membrane allowing objects to be inserted and withdrawn without undue loss of gas pressure at the site of the surgery. The manipulation of the body tube 17 up and down inserts the sac more deeply into or removes the sac upwardly from the abdominal wall W and the incision therethrough. As will be seen, the flexible sac 13 has an opening 22 adapted for specimen collection. The material of the sac 13 is rigid enough to hold its expanded shape, yet the sac is composed of a collapsible material permitting the sac to be folded or otherwise reduced in size to be confined within the cannula C. The body tube 17 serves as an actuating means connected to the sac 13 capable of displacing the sac longitudinally out of the space within the cannula C for specimen collection when expanded to the condition illustrated in FIGS. 1 and 2. The body tube 17 also serves, as will be appreciated, as an actuator adapted to draw the sac 13 out of the site of the surgery and through the incision in the body wall.

The body tube 17 is preferably provided with an internal passageway 23 which communicates with the space within the sac 13 itself. The internal passageway 23 may be utilized for the insertion of an elongated, rigid introducer shaft 30 (FIG. 1) for insertion lengthwise into and for lengthwise removal from the bore of the body tube 17. The shaft 30, movable back and forth within the elongated hollow rod 17, moves into and out of the receptacle 22 in the sac 13. The downward movement of the introducer 30 elongates or stretches the sac 13, allowing it to open up. Rotation of the sac, by rotating the body tube 17, helps the sac 13 to open up, especially if the introducer 30 is pulled back about half way.

It will be appreciated that the sac 13 is composed of a fluid-impermeable material and is thereby capable of retaining fluids as well as solid specimens and the like. Preferably, the sac 13 is entirely composed of blow-molded polymeric material capable of automatic expansion due to polymeric memory.

As will be apparent in FIGS. 1 and 2, the sac 13, when liberated, has an elongated configuration and the sac opening 22 extends along only a part of its length, particularly adjacent to the connection 16 to the body tube 17. The opening 22 is accordingly capable of being drawn into the confining space of the cannula C, by drawing the body tube 17 upwardly as viewed in FIGS. 1 and 2. This is an important feature of the invention as will further become apparent hereinafter.

Preferably, the sac 13 is composed of a material sufficiently flexible to allow the sac to be folded upon itself when it is intended to be positioned within the confining space within the cannula C. It is made of a non-reflective sheet material and does not cause blooming on the video screen or otherwise obscure the surgeon's view while the procedure is being conducted.

As is shown in FIG. 1, the optional seal 12, if used, forms a seal between the sleeve 17 and the (self-sealing) cannula C. Sealing in one form or another is of importance in view of the fact that many laparoscopic procedures are conducted while maintaining a positive gas pressure in the operative zone such as the abdomen or the like. The seal 12, if used, is instrumental in preserving the desired positive pressure. The cannula C may be any of a wide variety of cannulas but preferably embodies a slitted membrane such as shown in the U.S. Pat. to Knepshield et al No. 4,177,814, granted Dec. 11, 1979.

Although this invention is not limited to any particular dimensions, it is advantageous that the sleeve 17 may have an outside diameter of approximately 10 mm, which is convenient and practical because it is compatible with the inside diameters of existing cannulas and the like. Further, it is of advantage that, when the body tube 17 is hollow, the passageway therein may have an inside diameter of about 5 mm, thus allowing the insertion of standard diameter introducers or processing instruments such as grasping forceps.

The operative procedure in accordance with this invention will now become apparent. Presuming the incision has been made and the operative area insufflated to provide the desired gas pressure and that a cannula C (preferably self-sealing) has been introduced through the incision in abdominal wall W, the surgical collector and extractor of FIG. 1 is prepared by removing the seal 20 and the cap 11, and the surgical collector 10 is inserted vertically downwardly through the opening in the cannula C and through its seal, if any. The body tube 17 is then moved downwardly with respect to the cannula C to the desired position. Then, the introducer shaft 30 is moved downwardly against the bottom closed end of sac 13, tensioning sac 13 and allowing it to unfold itself to the expanded position of FIGS. 1 and 2.

The liberation of the sac 13 in the operative area causes the sac 13 to open of its own accord to a size larger than the cannula C. The opening movement also liberates the opening 22. The surgeon, working through this or another incision, performs the surgery and inserts one or more specimens or the like into the fluid-impermeable receptacle portion 26 of the sac 13. It is important that the material of the receptacle 26 is fluid impermeable, thus retaining not only the specimen or specimens introduced but any tissues or residues thereof or any fluids or other substances contained therein.

Once the collection of the specimen or specimens has been completed, the introducer shaft 30 may be withdrawn upwardly and removed from the sac 13, permitting it to contract or adapt to confining influences, following which the body tube 17 may be displaced upwardly, drawing the upper portion of the sac 13 into the confines of the cannula C. Continuing such upward movement until the entire sac opening 22 has been displaced upwardly within the confines of the cannula C, the contents of the receptacle portion 26 are sealed with respect to the cannula C. Following this, the surgeon can readily draw the receptacle portion 26 of the sac 13 upwardly with the material contained within the receptacle 26 intact and isolated from the operating area. Alternatively, by removing the cannula C through the incision, the filled sac 13 can directly contact and dilate the incision itself and can be removed completely without surgically excising the incision site. If the size of the specimen requires, the incision may however be enlarged.

It is important in accordance with this invention that the specimen is encased in a plastic or other sac which permits all of the fluids and tissue to be contained throughout the removal of the sac from the body cavity.

It is also important that the sac material should be rigid enough to hold its shape and provide an open orifice 22 throughout the procedure even when the sac 13 is rotated within the operating area as may be needed. Further, it is important that, in removing one or more large specimens, the sac 13 in accordance with this invention can be removed without surgically excising the incision site, and in some circumstances may be used simply to dilate the incision site to permit complete withdrawal from the body of the patient.

Although various kinds of strong bonds may be provided between the body tube 17 and the sac 13, the use of a solvent bond or heat shrunk juncture 16 is highly useful since dilation of the incision site may require the sac material and the connection between the sac and the body tube 17 to withstand a substantial force up to 50 pounds or more. For the same reasons, it is preferred to use a high strength plastic such as that used in intravenous bags as the material for the sac 13.

Although this invention has been described with reference to particular components and materials, it will be appreciated that wide varieties of changes and equivalents may be utilized, all without departing from the spirit and scope of this invention, which is defined in the appended claims.

What is claimed is:

1. A surgical collector and extractor for specimen collection and removal in a body cavity, comprising:
   (a) a substantially tubular elongated cannula having a confining space therein, said cannula being adapted for laparoscopic insertion through an incision into a body cavity and for removal from said cavity through said incision, (b) a sac of flexible material adapted to be confined within said confining space within said cannula, and having an opening adapted for specimen collection, (c) means for causing said sac to expand, when not confined, to form a receptacle having a size larger than said confining space, said means for expanding comprising rigidity of said material of said sac enough to hold its expanded shape, but collapsible to be confined within said cannula, and (d) a handle connected to said sac for displacing said sac into said confining space for specimen collection and for subsequently removing said sac from said body cavity, wherein said handle has an internal passageway extending into said sac.

2. The surgical collector and extractor defined in claim 1 wherein said handle is also adapted to draw said sac toward said confining space.

3. The surgical collector and extractor as defined in claim 2 wherein said material of said sac receptacle is composed of fluid-impermeable material and thereby capable of retaining fluids.

4. The surgical collector and extractor defined in claim 1 wherein said handle is an elongated rod, having said internal passageway.

5. The surgical collector and extractor defined in claim 4 further comprising an elongated introducer means movable back and forth in said internal passageway within said elongated rod and into and out of said receptacle in said sac for tensioning and allowing the opening of said sac.

6. The surgical collector and extractor as defined in claim 1 wherein said sac material is composed of blow molded polymeric sheet material capable of automatic expansion due to polymeric memory.

7. The surgical collector and extractor as defined in claim 1 wherein said sac has an elongated configuration and wherein said sac opening extends along only a part of the length of said sac.

8. The surgical collector and extractor as defined in claim 7 wherein said opening is located adjacent to said handle and is capable of being drawn into said cannula by drawing movement of said handle.

9. The surgical collector and extractor as defined in claim 1 wherein said sac material is made of non-reflective sheet material and is capable of being folded upon itself within said cannula.

10. The surgical collector and extractor as defined in claim 1 wherein said handle is a hollow tube having an outside diameter of about 10 millimeters.

11. The surgical collector and extractor as defined in claim 1 further comprising sealing means for sealing said confining space within said cannula when said sac is extended into said body cavity.

12. The surgical collector and extractor as defined in claim 11 wherein said sealing means extends between said cannula and said handle.

13. The surgical collector and extractor defined in claim 1 further comprising an elongated introducer means movable back and forth in said internal passageway within said handle and into and out of said receptacle in said sac for tensioning and allowing the opening of said sac.

14. A surgical collector and extractor for specimen collection and removal in a body cavity, comprising:

(a) a substantially tubular elongated cannula having a confining space therein, said cannula being adapted for laparoscopic insertion through an incision into a body cavity and for removal from said cavity through said incision, (b) a flexible sac adapted to be confined within said confining space within said cannula, and having an opening adapted for specimen collection, (c) a handle connected to said sac for displacing said sac into said confining space for specimen collection and for subsequently removing said sac from said body cavity, wherein said handle has an internal passageway extending into said sac, and (d) an elongated introducer shaft movable back and forth in said internal passageway within said handle and into and out of said sac for tensioning said sac, which allows said sac to expand when not confined to form a receptacle having a size larger than said confining space, said sac being formed of a material rigid enough to hold its expandable shape, but collapsible to be confined within said cannula.

* * * * *